(12) United States Patent
Shome et al.

(10) Patent No.: US 9,700,504 B2
(45) Date of Patent: Jul. 11, 2017

(54) COMPOSITION AND METHOD FOR AN INTRADERMAL HAIR GROWTH SOLUTION

(71) Applicants: Debraj Shome, Mumbai (IN); Rinky Kapoor, Mumbai (IN)

(72) Inventors: Debraj Shome, Mumbai (IN); Rinky Kapoor, Mumbai (IN)

( * ) Notice: Subject to any disclaimer, the term of this patent is extended or adjusted under 35 U.S.C. 154(b) by 48 days.

(21) Appl. No.: 14/409,115

(22) PCT Filed: Jun. 3, 2013

(86) PCT No.: PCT/IN2013/000354
§ 371 (c)(1),
(2) Date: Dec. 18, 2014

(87) PCT Pub. No.: WO2013/190567
PCT Pub. Date: Dec. 27, 2013

(65) Prior Publication Data
US 2015/0150771 A1    Jun. 4, 2015

(30) Foreign Application Priority Data

Jun. 19, 2012 (IN) .................... 2483/MUM/2011

(51) Int. Cl.
| | | |
|---|---|---|
| *A61K 8/64* | (2006.01) | |
| *A61K 8/67* | (2006.01) | |
| *A61K 8/44* | (2006.01) | |
| *A61K 31/7076* | (2006.01) | |
| *A61K 31/51* | (2006.01) | |
| *A61K 31/4415* | (2006.01) | |
| *A61K 31/375* | (2006.01) | |
| *A61K 31/122* | (2006.01) | |
| *A61K 31/07* | (2006.01) | |
| *A61K 31/714* | (2006.01) | |
| *A61K 38/30* | (2006.01) | |
| *A61K 38/06* | (2006.01) | |
| *A61K 38/18* | (2006.01) | |
| *A61K 38/22* | (2006.01) | |
| *A61K 8/60* | (2006.01) | |
| *A61Q 7/00* | (2006.01) | |
| *A61K 8/19* | (2006.01) | |

(52) U.S. Cl.
CPC .................. *A61K 8/64* (2013.01); *A61K 8/19* (2013.01); *A61K 8/44* (2013.01); *A61K 8/606* (2013.01); *A61K 8/67* (2013.01); *A61K 8/671* (2013.01); *A61K 8/673* (2013.01); *A61K 8/675* (2013.01); *A61K 8/676* (2013.01); *A61K 31/07* (2013.01); *A61K 31/122* (2013.01); *A61K 31/375* (2013.01); *A61K 31/4415* (2013.01); *A61K 31/51* (2013.01); *A61K 31/7076* (2013.01); *A61K 31/714* (2013.01); *A61K 38/06* (2013.01); *A61K 38/1825* (2013.01); *A61K 38/1866* (2013.01); *A61K 38/2292* (2013.01); *A61K 38/30* (2013.01); *A61Q 7/00* (2013.01)

(58) Field of Classification Search
None
See application file for complete search history.

(56) References Cited

U.S. PATENT DOCUMENTS

| | | | |
|---|---|---|---|
| 5,130,142 A | 7/1992 | Wong et al. | |
| 5,214,032 A | 5/1993 | Pickart et al. | |
| 5,252,559 A * | 10/1993 | Kronholm ................ | A61K 8/64 514/20.7 |
| 5,538,945 A * | 7/1996 | Pallenberg ............... | A61K 8/19 514/20.7 |
| 6,017,888 A | 1/2000 | Pallenberg et al. | |
| 6,030,948 A * | 2/2000 | Mann ....................... | A61K 8/41 514/20.7 |
| 6,502,699 B1 * | 1/2003 | Watson .................... | A61B 5/14 206/570 |
| 2004/0023855 A1 * | 2/2004 | John .................... | A61K 9/5161 424/130.1 |
| 2007/0224150 A1 * | 9/2007 | Chung .................... | A61K 8/64 424/70.14 |
| 2007/0231265 A1 | 10/2007 | Lin et al. | |
| 2007/0280924 A1 * | 12/2007 | Daniels et al. ...... | A61K 9/0048 424/94.61 |
| 2008/0312147 A1 * | 12/2008 | Azimi ....................... | A61K 8/19 514/6.9 |
| 2008/0317822 A1 * | 12/2008 | Azimi ....................... | A23L 2/52 424/439 |
| 2010/0278756 A1 | 11/2010 | Chung et al. | |

(Continued)

FOREIGN PATENT DOCUMENTS

| | | | | |
|---|---|---|---|---|
| CH | WO 2012042010 A1 * | 4/2012 | ....... | A61K 47/48038 |
| CN | 101919789 A | 12/2010 | | |

(Continued)

OTHER PUBLICATIONS

Paus Drug Discovery Today: Therapeutic Strategies 2006 3:101-110.*
Civas et al. The Journal of Dermatology 2010 37:823-826.*
Tsuboi Korean Journal of Investigative Dermatology 1997 492):103-108.*
Sugimoto et al. Journal of Investigative Dermatology 1995 104(5):775-778.*

(Continued)

*Primary Examiner* — Robert A Wax
*Assistant Examiner* — Caralynne Helm
(74) *Attorney, Agent, or Firm* — KramerAmado, P.C.

(57) ABSTRACT

Disclosed herein is an intradermal pharmaceutical composition for application to the scalp of a person for improving the bodily appearance comprising plurality of growth factors, peptides and nourishing complex in an amount effective to treat or to prevent hair loss by stimulating hair follicles and promoting hair growth, where such hair growth improves the bodily appearance of the said person.

20 Claims, 13 Drawing Sheets

(56) References Cited

U.S. PATENT DOCUMENTS

| | | |
|---|---|---|
| 2011/0112491 A1 | 5/2011 | Graham et al. |
| 2011/0306546 A1 | 12/2011 | Armani et al. |
| 2011/0313042 A1* | 12/2011 | Kramer ................ C07D 233/64 514/565 |
| 2013/0209551 A1* | 8/2013 | Luthy .............. A61K 47/48038 424/450 |

FOREIGN PATENT DOCUMENTS

| | | | | |
|---|---|---|---|---|
| KR | 20030031137 A | * | 4/2003 | ............. A61K 8/466 |
| KR | 20090070089 A | | 7/2009 | |
| NL | WO 9409750 A1 | * | 5/1994 | ............... A61K 8/44 |
| WO | WO 9625943 A1 | * | 8/1996 | ............... A61K 8/44 |
| WO | WO 2004043415 A1 | * | 5/2004 | ............... A61K 8/02 |
| WO | 2009062313 A1 | | 5/2009 | |

OTHER PUBLICATIONS

"International Search Report for PCT/IN2013/000354 dated Jul. 15, 2014".

\* cited by examiner

COMPOSITION AND METHOD FOR AN INTRADERMAL HAIR GROWTH SOLUTION

TECHNICAL FIELD OF THE INVENTION

The present invention relates to an intradermal pharmaceutical composition for prevention of hair loss and promotion of hair growth of mammalian hair. More specifically, it relates to an intradermal pharmaceutical composition of hair nourishing solution containing plurality of growth factors and biomimetic peptides for prevention of hair loss and promotion of hair growth.

BACKGROUND AND PRIOR ART

Hair loss is impacting job opportunities, relationships, mental wellbeing and self-confidence. It is common that, as people age, hair growth slows down. However, the phenomenon of hair loss can be due to many other causes also. Some of them are pathological or external or diet related, with effects on hair growth that vary depending on the evolution of the related disease or external event.

Alopecia (hair loss) can be classified as being one of two types: non-scarring alopecia and scarring alopecia. Non-scarring alopecia has been attributed to:
- Genetics and advanced age (i.e. androgenetic alopecia, female pattern hair loss)
- High fevers, severe infections, thyroid disease
- Childbirth, taking birth control pills
- Inadequate proteins or iron in diet
- Patients on drugs like blood thinners, treatments for gout, arthritis, depression, hypertension, chemotherapy
- Alopecia areata
- Physical or emotional stress
- Topical use of chemical treatments, such as hair dyes, permanent wave solutions, etc.
- Diseases, such as leprosy or syphilis
- Allergy Scarring alopecia may be a consequence of burns (accidental or post-surgical from cryosurgery or laser surgery) or trauma, which often causes destruction of hair follicles.

The most common cause of baldness or hair loss (95%) is however, the so called Androgenetic alopecia, that is the well-known tendency to baldness or thinning, developing in the twenty, thirty or forty aged persons.

For the purpose of the present invention, it is necessary to consider various types of hair, including terminal hair, vellus hair, and modified terminal hair such as in the eyebrows and eyelashes. Terminal hairs are coarse, pigmented, long hairs in which the bulb of the hair follicle is situated deep in the dermis. Vellus hairs, on the other hand, are fine, thin, non-pigmented short hairs in which the hair bulb is located superficially in the dermis. As alopecia progresses, a transition takes place in the area of approaching baldness wherein the hairs themselves are changing from the terminal to the vellus type. The size of the hair follicles is known to decrease.

Another factor that contributes to the end result is a change in the cycle of hair growth. In humans, each hair follicle undergoes repeated cyclical periods of growth. These cycles include anagen, an active growth stage, which can last for ~2 to 6 years; Catagen, a transition phase, which lasts for only ~1-2 weeks; and Telogen, a resting period which lasts ~3-4 months after which the hair is shed and a new hair is grown as the cycle repeats itself. In the normal human scalp, which contains approximately 100,000 hair follicles, 86% of the hair follicles are in Anagen, 1% is in Catagen, and 13% are in Telogen. Thus, under normal conditions, upto approximately 50-100 hairs may shed from the scalp each day. With the onset of male pattern baldness, a successively greater proportion of hairs are in the Telogen phase with correspondingly fewer in the active growth Anagen phase.

While a good deal is known about the results of male pattern baldness, very little is known about the cause. The cause is generally believed to be genetic and hormonal in origin. The known prior arts attempt to control it through hormone adjustment, but this has been singularly unsuccessful. Alopecia is associated with severe diminution of hair follicles. A bald human subject will have an average of only 306 follicles per square centimeter, whereas, a non-bald subject in the same age group will have an average of 460 follicles per square centimeter. This amounts to a one-third reduction in hair follicles which, when added to the increased proportion of vellus hair follicles and the increased number of hair follicles in the Telogen phase, is both significant and noticeable. Approximately, 50% of hair follicles must be shed to produce visible thinning of scalp hair. It is thus a combination of these factors: transition of hairs from terminal to vellus, increased number of Telogen hairs—some of which have been shed, and loss of hair follicles that produce 'baldness'.

So far, various approaches have been conceived to limit or remedy hair loss.

Surgical Techniques:
- Self-grafting or transplants—Hair bulbs are drawn from the posterior scalp that is hair-bearing and redistributed in a balding area.
- Flap surgery—A large horse shoe-shaped piece of scalp is partially detached from the donor fringe area and the free end is positioned over the bald spot where a corresponding patch of hair less scalp has been removed.
- Scalp reductions—A section of bald scalp is removed and the sides of scalp are lifted and sutured together, thereby reducing the overall surface area of the scalp.
- Scalp expansion and extension—Silicon bags are inserted beneath an area of hairy scalp and gradually inflated with saline water over a 6 week period. This causes the hair-bearing skin to stretch, thus increasing the amount of hair-bearing scalp. After removing the bags, expanded hair-bearing skin is lifted and moved to an adjacent bald area where similar sized patch of scalp has been excised.

Even though the use of laser and particular non-cicatrizing substances has reduced many chances of cicatrization, the surgical methods are costly, traumatic, painful and produce undesired side effects.

Non-Surgical Techniques:
These include additions of hair-bearing devices that can consist of human hair, synthetic fibre or a combination of both. These additions are attached by a variety of techniques, either the existing hair or skin being possible anchoring sites.

Medicinal Treatments:
Medicinal treatments include topical application of vasodilators like minoxidil, diazoxide etc. which cause the reactivation of cutaneous blood flow, thus producing the influx of oxygen and nutrients necessary for regeneration of tissues. One of the medications uses minoxidil as its active ingredient and is sold under the trade name Rogaine (a trademark of Pharmacia and Upjohn Company). Rogaine has shown to reduce hair loss and stimulate hair growth in upto 10% of men with male pattern baldness. Treatment with it though has to be exhaustively and regularly maintained. It is also very expensive. The topical application of substances used so far makes the ability of cutaneous absorption limited and superficial: that is unavoidable, given that, if the vasodilators should be absorbed in a massive manner, undesired systemic effects would arise.

Certain antiandrogens like Spironolactone, Aldactone, Cimetidine, or 5-alpha reductase inhibitors like oral Finasteride are known to avoid the transformation of testosterone to DHT which is responsible for hair loss. Finasteride is an active ingredient in Propecia (a trademark of Merck and Co. inc.) in pill form and has to be taken regularly. A drawback of antiandrogen therapy is that it is hard to restrict androgen blockage to the scalp only, thus causing undesired effects especially in men (decreased libido, impotence, gynaecomastia, etc.)

Thus, with regard to hair loss, the results obtained until now are not entirely satisfactory. Androgens (steroid hormones such as estrogen and testosterone) are the most obvious regulators of human hair growth in both sexes. Interestingly, androgens have contrasting effects on hair follicles depending on the hair follicle's location in the body. Androgens stimulate hair growth in many locations (i.e., beard, axilla) while inhibiting scalp hair growth in genetically predisposed individuals. Androgens act on the hair follicles via the dermal papilla, presumably by altering the production of regulatory factors (growth factors, peptides etc.) that influence the dermal papilla cells. Cultured dermal papilla cells secrete factors which are mitogenic for other dermal papilla cells, outer root sheath cells, epidermal keratinocytes and endothelial cells. Androgen-sensitive cells from beard or balding scalp reflect their in vivo androgenetic responses by responding to testosterone by either increasing (i.e., beard) or decreasing (i.e., balding) their mitogenic ability.

Many growth factors have been implicated in controlling different signals in the cycle of hair growth, with some playing major and some playing minor roles.

An article titled 'Growth factors and cytokines in hair follicle development and cycling: recent insights from animal models and the potentials for clinical therapy' by Danilenko et. al. published in Molecular medicine today, Volume 2, issue 11 discloses the importance of growth factors and cytokines in hair follicle development and cycling.

U.S. Pat. No. 5,538,945 relates to method for stimulating hair-growth in an animal by administering an effective amount of peptide copper complexes.

An article titled 'The effect of tripeptide-copper complex on human hair growth in vitro' By Pyo H K et. al. published in Arch Pharm Res. in 2007 discloses the effects of L-alanyl-L-histidyl-L-lysine-$Cu^{2+}$ (AHK-Cu) on human hair growth ex vivo and cultured dermal papilla cells. The results indicate that AHK-Cu promotes the growth of human hair follicles.

An article titled 'Control of hair growth and follicle size by VEGF-mediated angiogenesis' by Yano K et. al. published in J Clin Invest. 2001 February; 107(4):409-17 identifies VEGF as a major mediator of hair follicle growth and cycling and provides the evidence that improved follicle vascularization promotes hair growth and increases hair follicle and hair size.

WO/2007/102686 relates to a peptide having the activity of Insulin like growth factor-1 and a composition for improving skin conditions for treating a periodontal disease comprising the peptide.

An article titled 'Igf-I signaling controls the hair growth cycle and the differentiation of hair shafts' by Weger et. al. published in J Invest Dermatol. 2005 November; 125(5): 873-82 discloses the effects of Igf-I on follicular proliferation, tissue remodeling, and the hair growth cycle, as well as follicular differentiation.

An article titled 'Insulin-like growth factor 1 and hair growth' by Su el. al. published in Dermatology Online J. 1999 November; 5(2):1 discloses the effects of IGF-1 on follicle cell proliferation and differentiation, particularly, the paracrine versus endocrine action of IGF-1 on hair growth.

An article titled 'Hair growth induction: roles of growth factors' by Moore et. al. published in Ann NY Acad Sci. 1991 Dec. 26; 642:308-25 discloses the role of epidermal growth factor and fibroblast growth factor on hair growth induction.

An article titled 'Keratinocyte growth factor is an important endogenous mediator of hair follicle growth, development, and differentiation. Normalization of the nu/nu follicular differentiation defect and amelioration of chemotherapy-induced alopecia' by D. M. Danilenko et. al. published in Am J Pathol. 1995 July; 147(1): 145-154 investigates the effects of Keratinocyte Growth Factor on hair follicles in two distinct murine models of alopecia.

Despite the widespread occurrence of alopecia, especially androgenetic alopecia, the need for prevention and therapy still exists. There is a lot of ongoing research world over to develop a wonderdrug to treat this problem, though treatments from medications to surgery are currently available. However, not many benefit from existing treatments, sometimes they just do not work, there are a large number of unsatisfactory results, some patients are not suitable for available therapies, cost is huge for surgeries, results are not long lasting, side effects are a concern, etc. Therefore, there is still a need in the art for improved composition capable of preventing hair loss and stimulating hair growth.

It is therefore a principal object of the present invention to provide an intradermal pharmaceutical composition for effective treatment for prevention of hair loss and for stimulation of hair regrowth which is apparently non-toxic and relatively free of unwanted side effects.

Another object of the invention is to provide a treatment for male pattern alopecia which is safe, simple, painless, cosmetic in the sense of being invisible, easy to apply, and quite inexpensive when compared to hair transplants and the like.

Thus the invention described herein aims at resolving the problem of hair loss, a phenomenon which affects a wide portion of the population (especially the male one: nearly 2 out of 3 males develop some form of balding).

SUMMARY OF THE INVENTION

The present invention is directed to an intradermal pharmaceutical composition for application to the scalp of a person, for improving the bodily appearance, comprising plurality of growth factors, biomimetic peptides and additionally nourishing complexes in an amount effective to treat or prevent hair loss by stimulating hair follicles and promoting hair growth, where such hair growth improves the bodily appearance of the said person.

The intradermal pharmaceutical composition, formulated for intradermal injection to the subject, includes Vascular endothelial growth factor, basic fibroblast growth factor, insulin like growth factor 1, copper tripeptide 1, keratinocyte growth factor and thymosin-β4 additionally with vitamins, minerals, nucleic acids and amino acids, diluents and/or carriers.

In a further aspect, present invention provides a process for the synthesis of the formulation which includes adding the components in the right proportions of Vascular endothelial growth factor, basic fibroblast growth factor, insulin like growth factor 1, copper tripeptide 1, keratinocyte growth factor and thymosin β4 additionally with vitamins, minerals, nucleic acids and amino acids in a vehicle such as distilled water.

One or more hair growth promoting compounds selected from the group consisting of minoxidil, minoxidil analogues, minoxidil derivatives, anti-androgens and 5-alpha-reductase inhibitors may be co-prescribed with the pharmaceutical composition of the instant invention.

The composition of the present invention is used to prevent hair loss by stimulating hair follicles and promoting hair growth.

Figure 1:
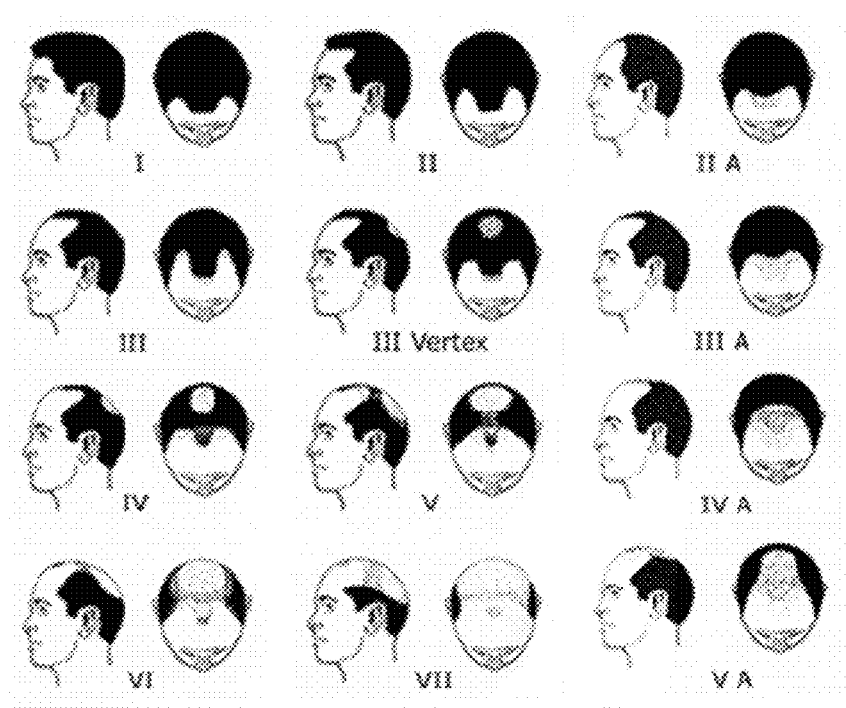
FIG. 1: Hamilton Norwood classification of Male pattern baldness.

The novel features which are considered characteristic for the invention are set forth in particular in the appended claims. Other aspects of the invention will become evident upon reference to the following detailed description. The invention itself, however, both as to its construction and its method of operation, together with additional objects and advantages thereof, will be best understood from the following description.

DETAILED DESCRIPTION OF THE INVENTION

In line with the object of present invention, there is provided an intradermal pharmaceutical composition for nourishment of hair follicles for preventing hair loss and stimulating hair regrowth in mammals.

As used herein the term 'effective amount' means an amount which stimulates hair growth associated with hair loss afflictions like male pattern baldness, or insults such as radiation or chemotherapy.

The term 'growth factor' relates to a naturally occurring protein capable of stimulating cellular growth, proliferation and cellular differentiation.

The term 'biomimetic peptide' as used herein relates to a synthetic agonist of naturally occurring growth factors and completely mimics the action of the parental molecules.

These peptides can provide clinical benefits similar to recombinant growth factors, reduce costs, and have greater chemical stability.

Accordingly, the present invention relates to an intradermal pharmaceutical composition for application to the scalp of a person for improving the bodily appearance comprising plurality of growth factors, biomimetic peptides and additionally nourishing complexes in an effective amount to treat or prevent hair loss by stimulating hair follicles and promoting hair growth, where such hair growth improves the bodily appearance of the said person.

The invention is based on two considerations:

1. Alopecia is a deficiency of terminal hair. In the bald person, there is a noticeable absence of terminal hair; though the skin does contain vellus hair which is the fine colorless hair which may require microscopic examination to determine its presence. This vellus hair is the precursor to terminal hair. Thus, the present invention relates to a method of treating the scalp to reduce hair loss and stimulate hair regrowth on the scalp.

2. Hair loss follows the alteration of microcirculation of the scalp. Its ongoing atrophy causes the loss of functionality of the hair follicle that becomes gradually unable to generate the hair. Like any tissue that slowly gets atrophic, the follicle which is no more supported by the microcirculation, (and thus by oxygen and nutrition) produces at first a fragile hair easy to tear at its root, and in the subsequent step includes spontaneous shedding of hair and the impossibility of its regeneration.

The epidermal hair follicles are regulated by interactions between the dermis and epidermis (the 2 layers of the skin), and undergo stages of growth (anagen), involution (catagen), and silence (telogen). Factors from the hair root which is present in the dermis, act as inducting signals for this cyclic growth of the hair. There are stem cells in an area of the hair follicle which pick up these signals and form a down growth into the dermis to form the hair shaft. A network of capillaries surrounding the base of the hair follicle delivers the nutrients—amino acids, vitamins, minerals—necessary for proper functioning. Cell division in the hair follicle is extremely fast. This rapid cell proliferation requires a constant supply of nutrients. The inducting signals for the hair follicle growth are the growth factors identified and components of the invention.

Many growth factors have been found to be responsible for the regulation of the hair growth cycle. The factors found to stimulate hair growth are insulin like growth factor 1, Basic fibroblast growth factor, vascular endothelial growth factor, thymosin β4, keratinocyte growth factor, copper tripeptide 1, noggin, follistatin, Wnt proteins, β catenin proteins, stem cell factor, prohairin β4, platelet derived growth factors. Analysis of several protein growth factors to find out which actually causes hair growth or the absence of which causes hair loss, and the optimum concentration required to get the desired result, resulted in the development of the said invention.

Accordingly, in an embodiment, the present invention provides an intradermal pharmaceutical composition that can stimulate the conversion of vellus hair to terminal hair as well as increase the rate of growth of terminal hair. Further, the intradermal pharmaceutical composition of the current invention prevents hair loss and stimulates the natural growth of hair in bald areas by restoring valid microcirculation to the scalp.

In an embodiment, the present invention discloses an intradermal pharmaceutical composition for the prevention of hair loss and to stimulate hair growth in a mammal, which includes in the following proportions of therapeutically acceptable ranges:
  i. Vascular endothelial growth factor (Human oligopeptide-11)—0.01 mg/L-100 mg/L
  ii. Basic fibroblast growth factor (Human oligopeptide-3)—0.01 mg/L-100 mg/L
  iii. Insulin like growth factor (Human oligopeptide-2)—0.01 mg/L-100 mg/L
  iv. Copper tripeptide 1—0.1 mg/L-500 mg/L
  v. Keratinocyte growth factor—0.01 mg/L-100 mg/L
  vi. Thymosin β4—0.005 mg/L-100 mg/L
along with pharmaceutically acceptable diluents and/or carriers.

The present invention further encompasses the compositions involving one or more known growth factors in addition to the composition of invention as mentioned above.

The known growth factors may be selected from the group consisting of noggin, follistatin, Wnt proteins, β catenin proteins, stem cell factor, prohairin β4 and platelet derived growth factors. Suitable carriers or diluents include but are not limited to distilled water, physiologic saline, bacteriostatic saline, (saline containing 0.9 mg/ml benzyl alcohol).

The present composition may additionally comprise vitamins selected from the group consisting of Vitamin A, Vitamin B1, Vitamin B2, Vitamin B3, Vitamin B5, Vitamin B6, Vitamin B7, Vitamin B10, Vitamin B12, Vitamin C, Vitamin K and Vitamin I, minerals selected from the group consisting of Sodium, Potassium, Magnesium and Calcium, nucleic acids selected from the group consisting of Adenosine, Cytosine, Guanine and Thymine and essential and non-essential amino acids selected from the group consisting of Taurine, Hydroxyproline, Methionine, Proline, Ornithine, Asparagine, Glutamic acid, Aspartic acid, Cystine, Serine, Glycine, Tyrosine, Phenylalanine, Isoleucine, Tryptophan, Threonine, Leucine, Histidine, Valine, Arginine, Lysine, Alanine and Glutamine.

The additional components may be present in the following therapeutically acceptable ranges: Vitamin A—0.01-0.50 mg/L, Vitamin B1—0.01-0.50 mg/L, Vitamin B2—0.01-0.50 mg/L, Vitamin B3—1.0-50 mg/L, Vitamin B5—0.001-0.050 mg/L, Vitamin B6—0.01-0.10 mg/L, Vitamin B7—0.001-0.050 mg/L, Vitamin B12—0.01-0.50 mg/L, Vitamin C—10-80 mg/L, Vitamin E—0.001-0.050 mg/L, Vitamin I—0.01-0.50 mg/L, Vitamin K—0.001-0.050 mg/L, Calcium salt—100-300 mg/L, Sodium salt—5000-7000 mg/L, Potassium salt—200-600 mg/L, Magnesium salt—10-200 mg/L, Nucleic acids each in the range of 1-50 mg/L, essential and non-essential amino acid in the range of 2-150 mg/L.

In a preferred embodiment, the present invention discloses an intradermal pharmaceutical a parenteral composition, which includes in the following proportions of therapeutically acceptable ranges:
i. Vascular endothelial growth factor (Human oligopeptide-11)—0.1 mg/L-10 mg/L
ii. Basic fibroblast growth factor (Human oligopeptide-3)—0.1 mg/L-5 mg/L
iii. Insulin like growth factor (Human oligopeptide-2)—0.1 mg/L-5 mg/L
iv. Copper tripeptide 1—1 mg/L-100 mg/L
v. Keratinocyte growth factor—0.1 mg/L-10 mg/L
vi. Thymosin β4—0.001 mg/L-1 mg/L
additionally along with vitamins, minerals, nucleic acids and amino acids, diluents and/or carriers along with pharmaceutically acceptable diluents and/or carriers. More preferably, the intradermal pharmaceutical composition for the prevention of hair loss and to stimulate hair growth in a mammal includes Vascular endothelial growth factor—5 mg/L, Basic fibroblast growth factor—2 mg/L, Insulin like growth factor—2 mg/L, Copper tripeptide 1-10 mg/L, Keratinocyte growth factor—1 mg/L and Thymosin β4—0.01 mg/L, along with pharmaceutically acceptable diluents and/or carriers.

The physical properties and the functions of the components in the composition of present invention are detailed below:
i. Vascular endothelial growth factor (VEGF), also called as Human Oligopeptide-11.
  Source: *E. coli*
  Appearance: White milky solution
  Purity: 95±1% (SDS-PAGE)
  Amino acid: 165 amino acids
  Molecular Weight: 19.2 kDa
  pH: 6.5±1.00
  Shape: Nanosome
  Preservative: Phenoxyethanol 0.2%
  Human VEGF 165, the most abundant form of VEGF, is a 23 kDa protein consisting of 165 amino acid residues. VEGF is a polypeptide growth factor and a member of the platelet-derived growth factor family.
Function:
1. Vascular endothelial growth factor (VEGF), essential for angiogenesis and vascular permeability, may be responsible for maintaining proper vasculature around the hair follicle during the anagen growth phase. The highest expression of VEGF is found in Dermal papilla cells, and, is also expressed by follicular keratinocytes of the outer root sheath.
2. It has been found to stimulate hair growth and increase hair size through facilitation of nutrient feeding to hair follicle by inducing angiogenesis (Ref. Kiichiro Y. et al., 2001, J. Clin. Invest. 107: 409-417).
ii. bFGF (basic fibroblast growth factor) also called Human Oligopeptide-3,
  Source: *E. coli*
  Appearance: White Milky Solution
  Purity: >95±1% (SDS-PAGE)
  Amino acid: 155 a.a
  Molecular Weight: 17.3 kDa
  pH: 6.5±1.00
  Shape: Nanosome
  Preservative: Phenoxyethanol 0.2%
Function:
1) It has ability to stimulate neovascularization, is a potent in vitro mitogen for capillary endothelial cells, and stimulates angiogenesis in vivo 2) This factor may regulate the mitotic activity of epithelially-derived cells
3) It is found in the Outer Root Sheath and in the region of the basal lamina of the follicle bulb, suggesting a role in bulb proliferation and fiber growth.
4) It affects hair follicle initiation and development.

iii. Insulin-like Growth Factor (IGF-1) also called Human oligopeptide-2.
  Source: *E. coli*
  Appearance: White Milky Solution
  Purity: >95±1% (SDS-PAGE)
  Amino acid: 70 a.a
  Molecular Weight: 7.6 kDa
  pH: 6.5±1.00
  Shape: Nanosome
  Preservative: Phenoxyethanol 0.2%

Recombinant Human IGF-I produced in *E. Coli* is a single, non-glycosylated, polypeptide chain containing 70 amino acids and having a molecular mass of 7655 Dalton. Dermal papilla cells are known to produce IGF1.

Function:
1) Insulin-like growth factor-I appears to sustain normal anagen growth. IGF-I affects follicular proliferation, tissue remodelling, and the hair growth cycle, as well as follicular differentiation. IGF-I signaling is an important mitogenic and morphogenetic regulator in hair follicle biology.
2) Androgen induction of follicular epithelial cell growth is mediated via insulin-like growth factor-I from dermal papilla cells.
3) Strengthen hair while stimulating hair follicles to produce strong hair shaft.

iv. Copper tripeptide-1
  Source: Chemical synthesis
  Appearance: Transparent Solution
  Purity: >90% (HPLC)
  Amino acid: 3 a.a
  Molecular Weight: 404 Da
  pH: 6.5±1.00
  Preservative: Phenoxyethanol 0.2%

Function:
1. Delivery of copper peptide to the base of follicles helps strengthen hair while stimulating hair follicles to produce strong hair shaft.
2. Increase follicle size.
3. Rebuilds the blood supply to damaged follicles, elevates the production of vascular endothelial growth factor.
4. Increases melanin synthesis, necessary to keep hair from turning white.
5. Increases subcutaneous fat below the scalp which seems to support function for the hair follicle.
6. Prolongs the hair growth phase.
7. Inhibits of 5-alpha reductase, the enzyme that reduces testosterone to DHT. DHT, in turn, is responsible for androgenetic alopecia. (Ref. H Uno. et al. 1995. Journal of Invest. Dermatology. 101: 143-147) inhibit the formation of DHT, hence reducing hair loss from male pattern balding in both men and women.
8. Reduces inflammation.

v. Keratinocyte Growth Factor (KGF) also called Human Oligopeptide 5.
  Source: *E. coli*
  Appearance: White Milky Solution
  Purity: >95±1% (SDS-PAGE)
  Amino acid: 163 a.a
  Molecular Weight: 18.9 kDa
  pH: 6.5±1.00
  Shape: Nanosome
  Preservative: Phenoxyethanol 0.2%

KGF is a member of the family of fibroblast growth factors, it is secreted in large amounts by fibroblast-like stromal cells in epithelial tissues.

Function:
1) Keratinocyte growth factor has been shown to regulate proliferation and differentiation in epithelial tissues and may regulate the clonogenic cells (stem cells) of the hair follicle.
2) Keratinocyte Growth Factor increases hair follicle survival following cytotoxic insult.
3) KGF stimulates capillary endothelial cell migration and proliferation and thus causes neovascularization. (*Journal of Cell Science* 112, 2049-2057 (1999)).
4) Helps strengthen hair while stimulating hair follicles to produce strong hair shaft.

vi. Thymosin β4
  Source: *E. coli*
  Appearance: Milky White Solution
  Purity: 95±1% (SDS-PAGE)
  Amino acid: 43 a.a
  Molecular Weight: 4.9 kDa
  pH: 6.5±1.00
  Shape: Nanosome
  Preservative: Phenoxyethanol 0.2%

Function:
1) Important mediator of cell migration and differentiation, it also promotes angiogenesis.
2) Thymosin β4 accelerates hair growth, in part, due to its effect on critical events in the active phase of the hair follicle cycle, including promoting the migration of stem cells and their immediate progeny to the base of the follicle, differentiation, and extracellular matrix remodeling.
3) Hepatocyte growth factor up-regulates thymosin β4 expression and may be acting by increasing thymosin β4 and/or synergizing with it.

The present pharmaceutical composition as described herein above is formulated for intradermal injection to the treatment area. Suitable vehicles for injection include, but are not limited to saline and distilled water.

The intradermal composition of the current invention is synthesized by a process including adding the components in the right proportions as mentioned above, additionally with the vitamins, minerals, amino acids, and nucleic acids, as mentioned in the entire composition of the solution, in a vehicle such as distilled water. The composition is then biologically sterilized and bottled into vials of 5 milliliter. The composition of the present invention is stable and can be stored at room temperature (below 25° C.).

The pharmaceutical composition is administered to a subject in a manner which will result in an effective delivery of the amount or dose of the ingredients to the area where hair growth is desired. Accordingly, the administration is effected by intradermal injections directly into the area where hair growth is desired, such as the scalp. The formulation is injected intradermally into the subject in the required amount per session; each session is performed once in 2 to 6 weeks, preferably once in 3 weeks.

The pharmaceutical composition is administered to a subject as follows:
a. cleaning the scalp of the subject with alcohol swab or surgical spirit;
b. treating the affected area of the scalp with pharmaceutical composition of growth factors in an effective stimulatory amount to treat or prevent alopecia.

In another embodiment, the intradermal composition is co-administered with one or more hair growth promoting compounds selected from the group consisting of minoxidil, minoxidil analogs, minoxidil derivatives, anti-androgens and 5 alpha-reductase inhibitors. The one or more hair growth promoting compounds mentioned above may be co-administered in the form of oral, liquid or topical administration.

One or more hair growth promoting compounds which is selected from the group consisting of minoxidil, minoxidil analogues, minoxidil derivatives, anti-androgens and 5-alpha-reductase inhibitors may be co-prescribed with the pharmaceutical composition.

The growth factors and biomimetic peptides of this invention may be used to stimulate hair growth in humans afflicted with androgenetic alopecia. Humans afflicted with this condition are usually male, and the condition results in loss of scalp hair with age, usually called male pattern baldness. Thus, these molecules may be administered in order to stimulate hair growth, thereby eliminating or reducing the severity of hair loss and/or the speed at which alopecia progresses. Other hair loss afflictions which can be treated include androgenetic alopecia, alopecia areata, female pattern baldness and secondary alopecia, and hair loss secondary to chemotherapy, radiation etc. (secondary alopecia). In the case of secondary alopecia, these may be used in advance of the hair loss insults such as chemotherapy or radiation regimens, to stimulating hair growth prior to the insults, thereby resulting in reduced amount of hair loss resulting therefrom. The pharmaceutical composition increases superficial cutaneous circulation in the subject, inhibits action of 5-α-reductase enzyme and thereby prevents hair loss by stimulating hair follicles and promoting hair growth.

The invention can be better understood by the following non-limiting examples. The examples given are mere an illustration of the instant invention and should not be construed as limiting the scope of the present invention in any manner.

EXAMPLES

Example 1

Preparation of the Intradermal Pharmaceutical Composition:

The growth factors and biomimetic peptides are imported They are then added in the desired proportions in combination with pharmaceutically/cosmetically acceptable and appropriate dose of vitamins, minerals, amino acids and nucleic acids, in a vehicle such as distilled water. The composition is then biologically sterilized and bottled into vials of 5 milliliter.

Example 2

5 mg of Vascular endothelial growth factor, 2 mg of Basic fibroblast growth factor, 2 mg of Insulin like growth factor, 10 mg of Copper tripeptide 1, 1 mg of Keratinocyte growth factor and 0.01 mg of Thymosin β4 additionally with pharmaceutically/cosmetically acceptable and appropriate dose of vitamins, minerals, amino acids and nucleic acids is added to 1 liter of distilled water. The composition is then biologically sterilized and bottled into vials of 5 milliliter each.

TABLE 1

Intradermal Pharmaceutical Composition

| Growth factors/peptides | Concentration |
| --- | --- |
| Vascular endothelial growth factor | 5 mg/L |
| Basic fibroblast growth factor | 2 mg/L |
| Insulin like growth factor | 2 mg/L |
| Copper tripeptide 1 | 10 mg/L |
| Keratinocyte growth factor | 1 mg/L |
| Thymosin β4 | 0.01 mg/L |
| Vitamins | q.s. |
| minerals | q.s. |
| amino acids | q.s. |
| nucleic acids | q.s. |
| carriers or diluents | q.s. |

Example 3

Stimulation of Hair Growth by Representative Growth Factors and Biomimetic Peptides in Mammals:

The following example indicates stimulation of hair growth in warm blooded animals after intradermal injection of representative growth factors and peptides of this invention. In this experiment, C3H mice were divided into 4 groups. The backs of the C3H mice, (60 days old, telogen hair growth phase) were closely clipped on day 1 with an electric clipper. A sterile solution of the pharmaceutical composition was then injected intradermally (i.e.: infiltrated under the skin) at 2 locations within the clipped areas of the mice. Injection at 2 locations provided 2 test locations within the clipped area of each mouse. Each injection (0.1 ml) contained different proportions of IGF 1, VEGF, bFGF, KGF, Thymosin β4 and copper tripeptide-1, in distilled water, labeled as solutions 1 through 4. A group of saline injected mice (0.1 ml) served as controls.

TABLE 2

|  | VEGF (mg/L) | bFGF (mg/L) | IGF -1 (mg/L) | Cu tripeptide 1 (mg/L) | KGF (mg/L) | Thymosin β4 (mg/L) |
| --- | --- | --- | --- | --- | --- | --- |
| Solution 1 | 0.01 | 0.01 | 0.01 | 0.1 | 0.01 | 0.005 |
| Solution 2 | 2 | 1 | 1 | 5 | 0.5 | 0.001 |
| Solution 3 | 5 | 2 | 2 | 10 | 1 | 0.01 |
| Solution 4 | 15 | 5 | 5 | 30 | 2 | 0.1 |

Following injection of the above intradermal pharmaceutical composition, indications of hair growth were seen within 10 days. The first visual signs were darkening of the skin in a circular region surrounding the injection site. The size of this region is generally dose dependent, increasing with an increase in dose to a certain extent. The 0.1 ml injections used in this experiment produced a circle of hair growth measuring approximately 0.5 cm$^2$ to 5 cm$^2$ in diameter. Active hair growth occurred between 14-20 days of the injection, with a maximum effect seen on day 30. Both the number of mice growing hair at the injection site and the diameter of hair growth region were determined on day 21. A positive response was observed with respect to the number of mice exhibiting hair growth at the injection sites compared to the total number of mice injected in the study. The results of this experiment are presented in Table 3 (The day of onset is the day at which hair follicle pigmentation was first observed).

Solution 3 comprising 0.0002 mg/0.1 ml of IGF1, 0.0002 mg of bFGF, 0.0005 mg of VEGF and 0.0001 mg of KGF, 0.001 mg of copper tripeptide and $1\times10^{-6}$ mg of Thymosin β4 within distilled water gave the best response. Increase in concentration of the ingredients beyond that in solution 4 did not give any significant benefit in terms of number of mice growing hair or the diameter of hair growth region.

TABLE 3

| Composition | Number of animals growing hair | Day of onset | Area of hair growth around the injection site |
|---|---|---|---|
| Solution 1 | 2/5 | 10 | <1 cm diameter |
| Solution 2 | 3/5 | 10 | >1 cm diameter |
| Solution 3 | 5/5 | 10 | >1 cm diameter |
| Solution 4 | 4/5 | 10 | >1 cm diameter |
| Solution 5 | 0 | NA | NA |

Example 4

Maintenance of Hair Follicle Viability by Intradermal Injection of the Pharmaceutical Composition in Secondary Alopecia:

The following experiment illustrates the localized maintenance of hair follicle viability (growth) by intradermal (local) injection of the pharmaceutical composition during treatment with chemotherapeutic agent cytosine arabinoside (Ara-C).

In this experiment, Sprague Dawley rat pups aged 8 days were maintained in 5 litters (n=10-12 per litter) for the duration of the study. On day 0, the litters received intradermal injection of the pharmaceutical composition in distilled water (solutions 1/2/3 or 4 as described in the example 3), or a saline control (1 injection per animal, 0.05 ml per injection). Each litter contained 2 normal control animals which received neither the pharmaceutical composition nor Ara-C, they received saline injection only. On day 1, the designated animals began a series of 7 consecutive daily intrapertioneal injections of Ara-C 25 mg/kg. On day 10, all animals were evaluated for the extent of hair loss at the injection sites. Using the rating identified as below:

Grade Degree of Alopecia 0 normal (no loss of hair)

1 slight thinning 2 moderate thinning 3 sparse hair cover 4 total loss of hair.

Ara-C injections caused significant hair loss by day 5-6 in most animals. In order to evaluate the stimulatory effect of the intradermal pharmaceutical composition, the degree of hair loss was evaluated at injected site daily. Injections containing the present composition generally caused retention of hair in a 0.25 cm radius around the injection site, most notably in the solution 3 group.

Table 4 presents the results as evaluated on day 10 using the previously described rating scale, with the degree of alopecia being expressed as the average response seen at the site of injection.

TABLE 4

| Composition | n = | Degree of alopecia (mean) |
|---|---|---|
| Saline only | 8 | 0.0 |
| Saline + Ara-C | 8 | 4.0 |
| Solution 1 + Ara-C | 8 | 3.25 |

TABLE 4-continued

| Composition | n = | Degree of alopecia (mean) |
|---|---|---|
| Solution 2 + Ara-C | 8 | 2.38 |
| Solution 3 + Ara-C | 9 | 1.44 |
| Solution 4 + Ara-C | 9 | 1.11 |

The observation of retained hair within the area of injection was examined histologically. While normal appearing and functional anagen hair follicles were observed at the site of injection of the pharmaceutical composition, follicles located away from the injection were dystrophic and non-functional (disruption of the integrity of inner and outer root sheaths, and disrupted hair shafts). These data confirm the gross observation of normal hair follicular function within the site of pharmaceutical composition injection, and illustrate the stimulatory effect of the intradermal pharmaceutical composition on hair follicle which maintains the active hair growth cycle during chemotherapy treatment.

Example 5

A double blind placebo controlled pilot clinical trial in 100 subjects with alopecia (male and female pattern hair loss) was done to evaluate safety and efficacy in the clinical application of the composition as an injectable for hair growth. Quantitative analysis of clinical microphotography and biopsies were utilized to evaluate treatment safety and efficacy. No adverse events were seen at any timepoint including at 1 year follow up. Statistically significant hair growth was seen in treated subjects at follow up after 8 treatments. In addition to the number of new hairs, a statistically significant ($p<0.05$) increase in hair density, which is directly related to the hair count over the treatment areas was also seen at 1 year timepoint. Other efficacy factors, such as hair thickness and terminal hair density, showed an upward trend at this timepoint as well. The pilot trial tested all 4 formulations and although one formulation (solution 3) was found to be superior, hair regrowth was seen in all groups.

On an average, after the fourth session, the hair loss stops and scalp starts appearing more trophic. After about 8 sessions the hair growth process was self-evident. The regrowth process was consistent, so that after a year from the beginning, strong hair was present in about 90% of the affected scalp in most cases. The new hair was resistant to traction.

This shows that the present invention not only results in rapid hair growth (statistically significant increase in the number of terminal hairs, hair thickness, density, and hair shaft diameter was seen after completion of 8 sessions), but that these results persist over some time. Other non-surgical treatments not only give limited hair growth but also, new hair is lost very shortly after discontinued use.

Example 6

Quantity of Injection: 1 ml Per Session

Mode of administration: Administered by a 1 cc disposable syringe having a 26-30 gauge needle used to intradermally inject 1 ml of the said solution. Ideally, multiple injections are given, each measuring 0.01 ml, such that the desired quantity of 1 ml is uniformly distributed throughout the affected area of the scalp.

Frequency of injection: It is obvious that, in order to obtain satisfactory and lasting results, given that at any given time, different hair follicles are in various stages of hair growth cycle, a sequence of injections will be necessary, a reasonable way to proceed consists of injections repeated 3 weekly for about 8 sessions, as inferred from the above examples.

Example 7

Figure 2:
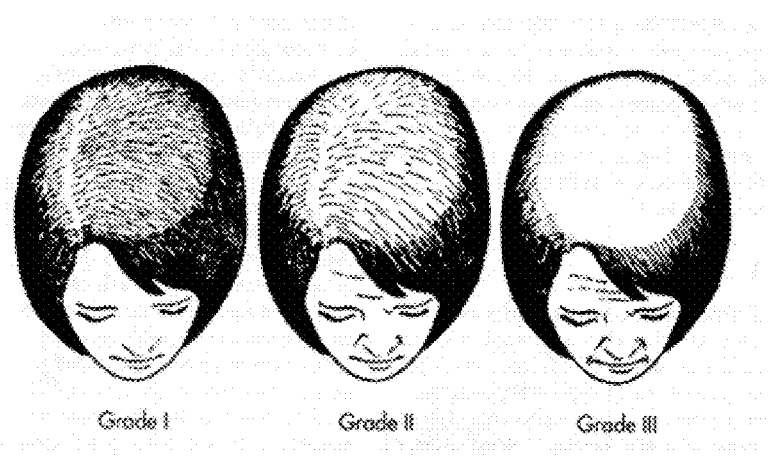
FIG. 2: Ludwig classification of Female pattern baldness.
In all figures below—Blue/Series 1=baseline, red/Series 2=after 4 sessions, green/Series 3=after 8 sessions

A clinical study was conducted to investigate the efficacy of the intradermal composition in enhancing human hair growth. A total of 750 patients (men and women, 20-60 years of age) were chosen for the study. The patients included:

1. stubborn hair loss cases who had not responded to 1 year or more of conventional therapy,
2. post hair transplant hair loss cases,
3. males with Norwood Hamilton grades II to VI as shown in FIG. 1, and females with Ludwig all 3 grades as shown in FIG. 2, A demographic data of first 100 patients included in the study is provided in Table 5.

TABLE 5

| Sr. No | Age | Sex | Hair colour | Baseline diagnosis | Duration in study | H/o hair loss | other medical condition | addiction | Previous treatment |
|---|---|---|---|---|---|---|---|---|---|
| 1 | 53 | M | majority black | AGA III | 24 weeks | 7 years | hypertension | tobacco chewing | Minoxidil(M) 5%, finasteride (F) 1 mg |
| 2 | 45 | M | majority black | AGA III vertex | 24 weeks | 5 years | | smoking | homeopathy |
| 3 | 36 | F | black | FPHL 2 | 24 weeks | 3 years | hypothyroid | | |
| 4 | 62 | M | gray | AGA V | 24 weeks | 15 years | hyper-cholesterolemia, hypertension | occasional alcohol | M5% |
| 5 | 28 | M | black | AGAIII vertex | 24 weeks | 8 years | | occasional smoking | M5%, multivitamin tablets, ayurvedic |
| 6 | 39 | F | black brown | FPHL 1 | 24 weeks | 2 years | post pregnancy initiation of hair loss | | |
| 7 | 34 | M | black | AGA III | 24 weeks | 10 years | | | 1 session of hair transplant 1 year ago |
| 8 | 29 | M | black | AGA II | 24 weeks | 4 years | | occasional alcohol | home remedies |
| 9 | 30 | F | black brown | FPHL 2 | 24 weeks | 5 years | Polycystic ovarian disease | | oral contraceptives |
| 10 | 57 | M | gray | AGA IV | 24 weeks | 15 years | hypertension, diabetes | smoking | M5%, F 1 mg |
| 11 | 41 | M | majority gray | AGA III vertex | 24 weeks | 6 years | hypertension | occasional alcohol | M5%, multivitamins |
| 12 | 50 | M | Majority gray | AGA IV | 24 weeks | 10 years | hyper-cholesterolemia, diabetes | occasional smoking, tobacco chewing | Hair transplant 2 years ago |
| 13 | 33 | F | black | FPHL 1 | 24 weeks | 6 years | anemia | | Homeopathy |
| 14 | 25 | M | black | AGA III | 24 weeks | 4 years | depression | Smoking | M5%, F1 mg |
| 15 | 37 | M | majority black | AGA IV | 24 weeks | 7 years | hypertension | alcohol | topical steroids, M2%, vitamins |
| 16 | 45 | F | Majority black | FPHL 1 | 24 weeks | 3 years | Menopause | | M2% |
| 17 | 38 | M | Majority gray | AGA IV | 24 weeks | 8 years | diabetes | | M2%, F 1 mg |
| 18 | 20 | F | black | FPHL 2 | 24 weeks | 4 years | Polycystic ovaries, hypothyroid | | Oral contraceptives, M2% |
| 19 | 49 | M | Majority gray | AGA IIIA | 24 weeks | 6 years | hyper-cholesterolemia | occassional smoking | M5% |
| 20 | 36 | M | Majority black | AGA IIIA | 24 weeks | 5 years | | | M5%, F 1 mg, vitamins, spa treatments |
| 21 | 52 | F | Majority black | FPHL2 | 24 weeks | 4 years | Menopause | | Spa treatments |
| 22 | 63 | M | Majority gray | AGA V | 24 weeks | 20 years | diabetes | smoking | M5%, F 1 mg |
| 23 | 50 | M | Majority gray | AGA IV vertex | 24 weeks | 10 years | hypertension | occasional alcohol | M 5% |
| 24 | 29 | M | black | AGA IV | 24 weeks | 10 years | | | ayurvedic, homeopathy, M55, F 1 mg |
| 25 | 28 | F | black | FPHL 1 | 24 weeks | 3 years | anemia | | |
| 26 | 32 | M | black | AGA IV | 24 weeks | 6 years | | occasional smoking | hair transplant 6 months ago |
| 27 | 66 | M | gray | AGA IV | 24 weeks | 18 years | hypertension, diabetes | alcohol | M5% |
| 28 | 34 | F | black | chronic Telogen effluvium | 24 weeks | 4 years | post typhoid non responding hair loss | | Vitamins |

TABLE 5-continued

| Sr. No | Age | Sex | Hair colour | Baseline diagnosis | Duration in study | H/o hair loss | other medical condition | addiction | Previous treatment |
|---|---|---|---|---|---|---|---|---|---|
| 29 | 44 | M | black | AGA IV | 24 weeks | 6 years | | | M5% |
| 30 | 35 | M | black | AGA III | 24 weeks | 2 years | | occasional smoking | |
| 31 | 24 | M | black | AGA II | 24 weeks | 2 years | | | |
| 32 | 38 | M | black | AGA IV | 24 weeks | 7 years | Hypertension | | M5% |
| 33 | 47 | F | majority black | Lichen planus of scalp | 24 weeks | 1 year | Lichen planus body | | topical steroids, M2% |
| 34 | 30 | M | black | AGA III | 24 weeks | 2 years | | Smoking | aminexil |
| 35 | 40 | M | majority black | AGA IV | 24 weeks | 5 years | | | aminexil, M5% |
| 36 | 37 | F | black | FPHL 1 | 24 weeks | 5 years | anemia | | vitamin supplements |
| 37 | 43 | M | majority black | AGA IV vertex | 24 weeks | 6 years | hyper-cholesterolemia | occasional smoking | artificial hair fibre |
| 38 | 35 | M | black | AGA III vertex | 24 weeks | 3 years | | occasional alcohol | |
| 39 | 41 | M | majority black | AGA IV | 24 weeks | 10 years | | | M5% |
| 40 | 20 | M | black | AGA II | 24 weeks | 1 year | | | |
| 41 | 36 | M | black | AGA III vertex | 24 weeks | 3 years | | | |
| 42 | 29 | M | black | AGA IV | 24 weeks | 5 years | | Occasional smoking | M2% |
| 43 | 35 | F | black | post pregnancy initiation of hair loss | 24 weeks | 4 years | anemia | | M2% |
| 44 | 40 | M | Majority black | AGA IV | 24 weeks | 10 years | | | Homeopathy |
| 45 | 39 | M | Majority black | AGA IV | 24 weeks | 5 years | Hypertension | occasional alcohol | Homeopathy |
| 46 | 27 | M | black | AGA III vertex | 24 weeks | 6 years | | | M5% |
| 47 | 28 | M | black | AGA III vertex | 24 weeks | 4 years | | smoking | vitamins |
| 48 | 47 | M | black | AGA V | 24 weeks | 11 years | Diabetes | occasional alcohol | M5%, F 1 mg |
| 49 | 39 | M | black | AGA IV vertex | 24 weeks | 8 years | Hypertension | | Home remedies |
| 50 | 34 | F | brown | FPHL 2 | 24 weeks | 5 years | | | homeopathy |
| 51 | 35 | F | black | FPHL 1 | 24 weeks | 3 years | hypothyroid | | |
| 52 | 50 | M | majority black | AGA III | 24 weeks | 8 years | hypertension | occasional alcohol | M5% |
| 53 | 43 | M | Majority gray | AGA V | 24 weeks | 6 years | hyper-cholesterolemia | | M5%, F 1 mg |
| 54 | 36 | F | black | Lichen planus early | 24 weeks | 5 years | | | M2%, homeopathy |
| 55 | 35 | M | black | AGA IV | 24 weeks | 7 years | | | M2% |
| 56 | 22 | M | black | AGA III | 24 weeks | 2 years | | | |
| 57 | 37 | M | majority black | AGA IV | 24 weeks | 4 years | | smoking | M2%., F 1 mg |
| 58 | 36 | M | Black | AGA V | 24 weeks | 9 years | | occasional alcohol | hair transplant 3 years ago |
| 59 | 35 | F | black | FPHL 1 | 24 weeks | 3 years | | | |
| 60 | 45 | M | Majority black | AGA IV vertex | 24 weeks | 10 years | hypertension | occasssional alcohol | M2% |
| 61 | 48 | M | Majority gray | AGA V | 24 weeks | 12 years | diabetes | tobacco chewing | hair transplant 5 years ago |
| 62 | 26 | M | black | AGA III | 24 weeks | 3 years | | | vitamins |
| 63 | 36 | M | black | AGA IV | 24 weeks | 5 years | asthma | occasional alcohol | M5%, F 1 mg |
| 64 | 55 | M | black | AGA IV vertex | 24 weeks | 7 years | hyper-cholesterolemia | | M 5%, F 1 mg |
| 65 | 47 | M | majority black | AGA IV | 24 weeks | 12 years | hypertension | occasional smoking | M5% |
| 66 | 33 | F | black | FPHL 1 | 24 weeks | 5 years | anemia | | |

TABLE 5-continued

| Sr. No | Age | Sex | Hair colour | Baseline diagnosis | Duration in study | H/o hair loss | other medical condition | addiction | Previous treatment |
|---|---|---|---|---|---|---|---|---|---|
| 67 | 37 | F | black | loose anagen syndrome | 24 weeks | 15 years | | | vitamins, topical steroids |
| 68 | 43 | M | black | AGA IV | 24 weeks | 6 years | | | M5% |
| 69 | 52 | M | Majority gray | AGA V | 24 weeks | 12 years | hypertension | Smoking | M5%, F 1 mg, Homeopathy |
| 70 | 38 | F | Majority black | FPHL 2 | 24 weeks | 10 years | hypertension, hypothyroid | | home remedies |
| 71 | 36 | M | black | AGA IV | 24 weeks | 8 years | | | F 1 mg, vitamins |
| 72 | 48 | M | majority black | AGA III vertex | 24 weeks | 10 years | Hypertension | smoking | M5%, F 1 mg |
| 73 | 32 | M | black | AGA IV | 24 weeks | 6 years | | alcohol | ayurvedic, |
| 74 | 26 | F | black | FPHL 1 | 24 weeks | 3 years | Polycystic ovaries, | | |
| 75 | 28 | F | black | chronic Telogen effluvium | 24 weeks | 5 years | | | M2% |
| 76 | 36 | F | black brown | chronic telogen effluvium | 24 weeks | 7 years | multiple treatments for IVF | | vitamins |
| 77 | 35 | F | black | FPHL 2 | 24 weeks | 5 years | Hypothyroid | | M2% |
| 78 | 34 | M | black | AGA V | 24 weeks | 8 years | | | M5%, F 1 mg |
| 79 | 36 | M | black | AGA IV | 24 weeks | 5 years | | smoking | M5% |
| 80 | 40 | M | majority black | AGA IV vertex | 24 weeks | 7 years | hyper-cholesterolemia | occasional smoking | |
| 81 | 45 | F | Majority gray | FPHL 2 | 24 weeks | 10 years | hypertension | | M2% |
| 82 | 46 | M | Majority gray | AGA IV vertex | 24 weeks | 7 years | | | M5% |
| 83 | 54 | M | Majority gray | AGA IV | 24 weeks | 6 years | Diabetes | | M5%, F 1 mg |
| 84 | 34 | F | black | Chronic telogen effluvium | 24 weeks | 3 years | | | M2% |
| 85 | 45 | M | majority black | AGA III vertex | 24 weeks | 6 years | Hypertension | Smoking | M5%. F 1 mg |
| 86 | 30 | F | black | FPHL 1 | 24 weeks | 3 years | Polycystic ovarian disease | | |
| 87 | 42 | F | black | FPHL 2 | 24 weeks | 8 years | | Smoking | M2%, aminexil |
| 88 | 39 | M | Majority black | AGA IV | 24 weeks | 10 years | Diabetes | Occasional alcohol | M5%, aminexil |
| 89 | 44 | M | Majority black | AGA V | 24 weeks | 12 years | Hypertension | Occasional alcohol | M5%, F 1 mg |
| 90 | 37 | F | Majority black | Chronic telogen effluvium | 24 weeks | 7 years | | | vitamins |
| 91 | 56 | M | Majority gray | AGA IV vertex | 24 weeks | 13 years | hyper-cholesterolemia | occasional alcohol | M2% |
| 92 | 41 | F | Majority black | FPHL3 | 24 weeks | 12 years | Polycystic ovarian disease, hypothyroid | | M2%, aminexil, topical staeroids |
| 93 | 44 | M | Majority black | AGA V | 24 weeks | 9 years | hypertension | | Hair transplant 2 years ago |
| 94 | 32 | M | black | AGA III | 24 weeks | 5 years | | | M2% |
| 95 | 46 | M | majority black | AGA IV | 24 weeks | 6 years | | occasional smoking | vitamins, home remedies |
| 96 | 42 | F | majority black | FPHL 2 | 24 weeks | 10 years | hyper-cholesterolemia | | M2%, hair transplant 3 years ago |
| 97 | 32 | F | black | FPHL 1 | 24 weeks | 3 years | | | M2% |
| 98 | 39 | F | majority black | Lichen planus early | 24 weeks | 5 years | lichen planus body | | topical steroids, M2% |

TABLE 5-continued

| Sr. No | Age | Sex | Hair colour | Baseline diagnosis | Duration in study | H/o hair loss | other medical condition | addiction | Previous treatment |
|---|---|---|---|---|---|---|---|---|---|
| 99 | 38 | M | majority black | AGA IV | 24 weeks | 6 years | hypertension | occassional alcohol | M5% |
| 100 | 56 | M | majority gray | AGA V | 24 weeks | 10 years | diabetes | | M5%, F 1 mg |

Abbreviations used in Table 5:
M = male
F = Female
M2% = minoxidil solution 2%
M5% = minoxidil solution 5%
F (1 mg) = Finasteride tablet (1 mg)
AGA = Androgenetic alopecia
FPHL = Female pattern hair loss All patients were advised to be on topical minoxidil (2% in case of females and 5% in case of males) regularly along with oral 1 mg finasteride for males. Other medications were required to be withdrawn 6 months before the study and were not permitted during the study. The study protocol was approved by the appropriate institutional review board, and each patient signed a written consent form before participating in the study.

The intradermal pharmaceutical composition was injected with an insulin syringe about 1-1.5 ml per session by the Nappage technique across the scalp where there is visible thinning. 8 such sessions were performed for each patient, at 3 weekly intervals. At each visit, adverse experiences were recorded, and a medical examination was performed.

a) Global Photographic Assessment:

Standardized clinical photographs of the head for clinical assessment were taken at session 4 and session 8, and 2 months after session 8. The vertex and superior frontal areas of the scalp were photographed using a standardized technique. Photographs were assessed by 3 independent dermatologists who compared the pre and post treatment appearance of the scalp using a 10-point scale.

b) Videomicroscopic Assessment:

Videomicroscopic photographs were also taken with the Proscope digital hand held camera at fixed positions on the central scalp, 15 cm and 20 cm posterior to the glabella. At each fixed position images were taken through both 0.25 cm and 0.5 cm windows to calculate hair counts per $cm^2$. All videomicroscopic images were analyzed for changes in vellus hair count, terminal hair count and hair shaft diameter using specialized software using specialized software (Trilogic Company, Moscow, Russia; Tricho science version 1.5 has been available since 2008 through Merz Pharmaceuticals, Frankfurt, Germany). Paired t-testing of the data was performed.

c) Subjective Analysis:

All before and after videomicroscopic and clinical images were randomized and graded subjectively by three blinded reviewers. Reviewers were instructed to grade each image from 0 to 10, where 0 represented no growth and 10 indicated full, thick hair growth. Both the clinical and video microscopic scores were averaged and compared before and after.

d) Patient Self-Assessments

Patients completed a validated, self-administered hair growth questionnaire comprising seven questions, four relating to efficacy of treatment and three to satisfaction with appearance of scalp hair (Table 6). Patients completed a hair growth questionnaire, and investigators rated the change in hair appearance compared with baseline, at the sessions mentioned above. The translation of the questionnaires and the responses were scored, with a score of 1 assigned to the most positive response. For the statistical analysis, scores were centered on 0 (neutral response), and improvement was assigned the positive numbers.

TABLE 6

| Sr. No. | Question | Possible responses |
|---|---|---|
| 1 | Since the start of the study, I can see my bald spot getting smaller | Strongly agree(1.).>Strongly disagree (5) |
| 2 | Because of the treatment I have received since the start of the study, the appearance of my hair is: | A lot better (1.).>A lot worse (7) |
| 3 | Since the start of the study, how? would you describe the growth of your hair | Greatly increased (1.).>Greatly decreased (7) |
| 4 | Since the start of the study, how effective do you think the treatment has been in slowing down your hair loss? | Very effective (1.).>Not effective at all (4) |
| 5 | Compared to the beginning of the study, which statement best describes your satisfaction with the appearance of: | |
| | a) the hairline at the front of your head? | Very satisfied (1.).>Very dissatisfied (5) |
| | b) the hair on top of your head? | Very satisfied (1.).>Very dissatisfied (5) |
| | c) your hair overall? | Very satisfied (1.).>Very dissatisfied (5) | e) Safety Assessments:

Medical history of the patient was recorded at the screening visit and a complete physical examination was performed. Safety assessments included physical examination and non leading questioning about adverse experiences at each visit, as well as periodic laboratory evaluations.

f) Laboratory Evaluations:

Hematology and serum biochemical analysis were performed at baseline, and sessions 4 and 8 and 2 months post $8^{th}$ session in cases which required it.

Figure 3:
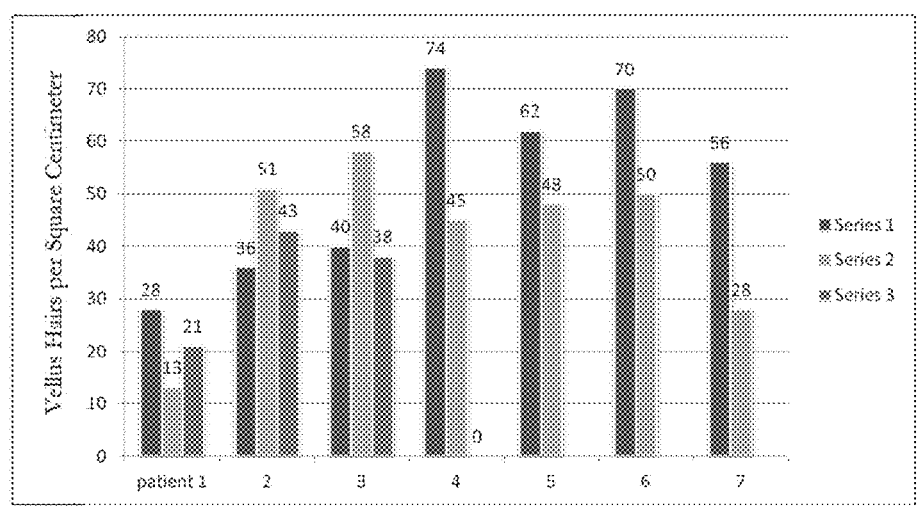
FIG. 3: Chart for Vellus hair counts at 15 cm after 4th session (shown for 7 patients).

Results:

The presence of a dose response was tested by linear regression analysis (including study center effect) for all efficacy endpoints.

i. Vellus Hair Counts:

Vellus hair counts for each patient, taken at 15 cm from the glabella, are depicted in FIG. 3 (only 7 patients shown here). Overall, 86% had a decrease in the number of vellus hairs, while remaining patients had an increase. Paired t-testing indicated that, on average, the patients after 4 sessions had 8.57 fewer vellus hairs and 11.57 fewer vellus hairs after 8 sessions, than at baseline. This was statistically significant.

Figure 4:
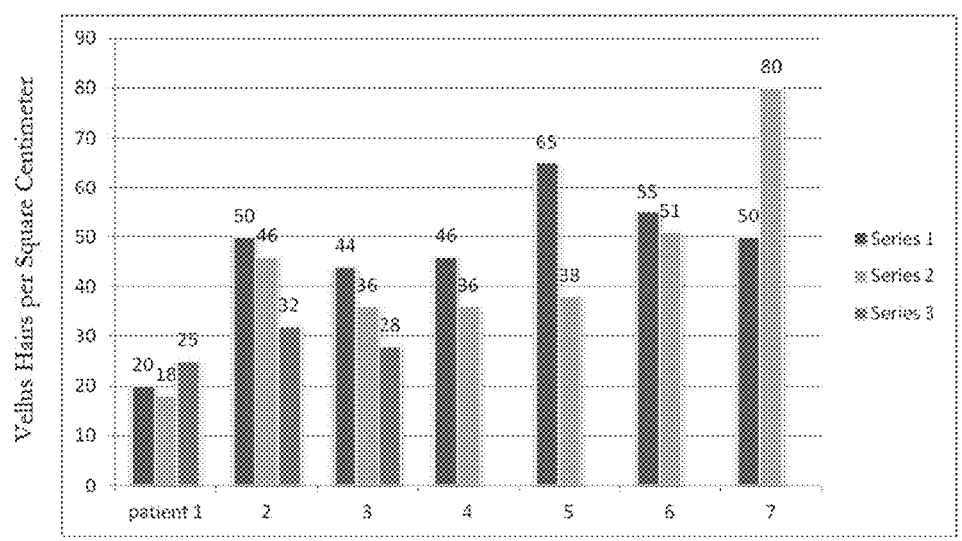
FIG. 4: Chart for Vellus hair counts at 20 cm from glabella after 4th session (shown for 7 patients).
Figure 5:
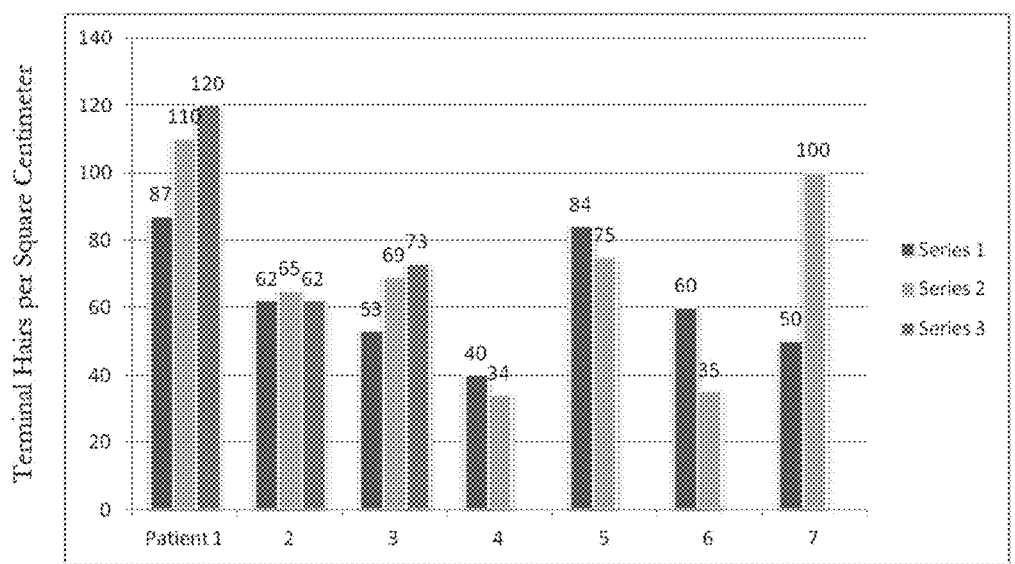
FIG. 5: Chart for Terminal hair counts at 15 cm from glabella after 4 sessions (shown for 7 patients).

Vellus hair counts, taken at 20 cm from the glabella, are depicted in FIG. 4. 71% patients had a decrease in the number of vellus hairs, while remaining patients had an increase. Paired t-testing indicates that, on average, the patients after 4 sessions had 3.29 fewer vellus hairs, and after 8 sessions had 7.29 few vellus hairs than at baseline. Again, this was statistically significant.

ii. Terminal Hair Counts:

Terminal hair counts for each patient, taken at 15 cm from the glabella, are depicted in FIG. 5. 80% patients had an increase in the number of terminal hairs, while others patients had a decrease. Paired t-testing indicates that, on average, the patients after 4 sessions had 7.57 more terminal hairs, and after 8 sessions had 14.57 more terminal hairs than at baseline. This was statistically significant.

Figure 6:
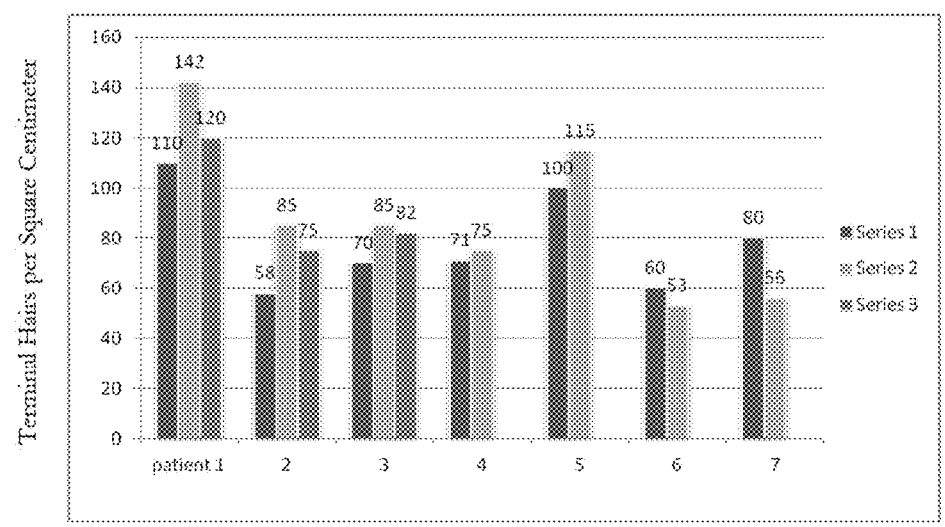
FIG. 6: Chart for Terminal hair counts at 20 cm from glabella after 4 sessions (shown for 7 patients).
Figure 7:
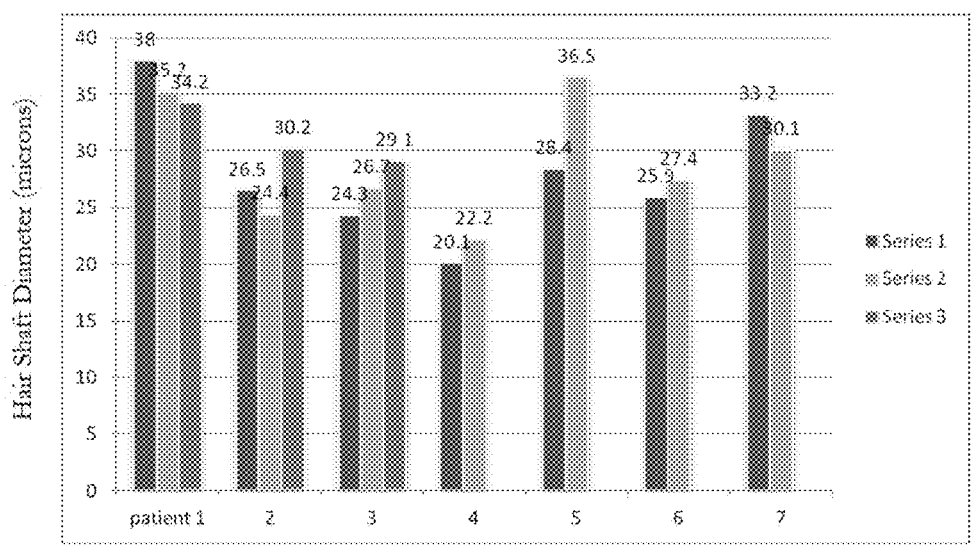
FIG. 7: Chart for Hair shaft diameter at 15 cm from glabella after 4 sessions (shown for 7 patients).

Terminal hair counts for each patient, taken at 20 cm from the glabella, are depicted in FIG. 6. 70% patients had an increase in the number of terminal hairs, while other patients had a decrease. Paired t-testing indicates that, on average, the patients after 4 sessions had 6.14 more terminal hairs, and after 8 sessions had 8.15 more terminal hairs than at baseline.

iii. Hair Shaft Diameter:

The average hair shaft diameter for each patient, taken at 15 cm from the glabella, is depicted in FIG. 7. 57% patients had an increase in the width of their hairs, while remaining patients had a decrease. Paired t-testing indicated that after 4 sessions, patients had an average hair shaft diameter that was 1.0 µm wider and 5 µm wider after 8 sessions than at baseline. This was statistically significant.

Figure 8:
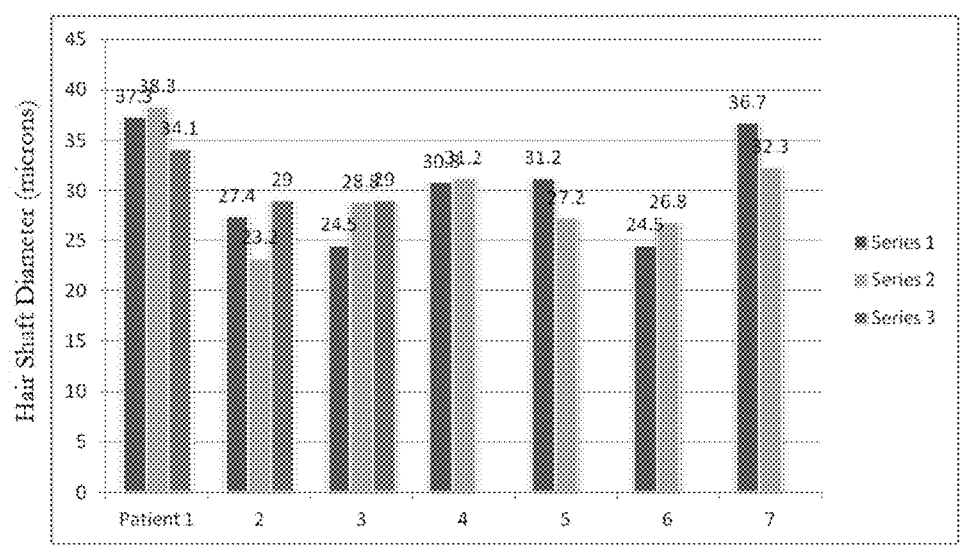
FIG. 8: Chart for Hair shaft diameter at 20 cm from glabella after 4 sessions (shown for 7 patients).

The average shaft diameter, taken at 20 cm from the glabella, is depicted in FIG. 8. Paired t-testing indicated that after 4 sessions patients had an average hair shaft diameter that was 0.97 µm wider, and after 8 sessions average hair shaft diameter was 3.03 um wider than at baseline. This was statistically significant.

Table 7 summarises the above data for Vellus and Terminal hair counts and hair shaft diameters.

TABLE 7

| | Mean at baseline | Mean after 4 sessions | Mean after 8 sessions | delta | p-value |
|---|---|---|---|---|---|
| Vellus hair counts at 15 cm | 52.43 | 43.86 | 40.86 | −11.57 | 0.003131 |
| Vellus hair counts at 20 cm | 48.86 | 45.57 | 41.57 | −7.29 | 0.006474 |
| Terminal hair counts at 15 cm | 64.14 | 71.71 | 78.71 | −14.57 | 0.004183 |
| Terminal hair counts at 20 cm | 82.14 | 88.29 | 90.29 | −8.15 | 0.004441 |
| Hair shaft diameter at 15 cm (µm) | 27.98 | 28.98 | 32.98 | −5 | 0.006361 |
| Hair shaft diameter at 20 cm (µm) | 29.74 | 30.71 | 32.77 | −3.03 | 0.005161 |

Figure 9A:
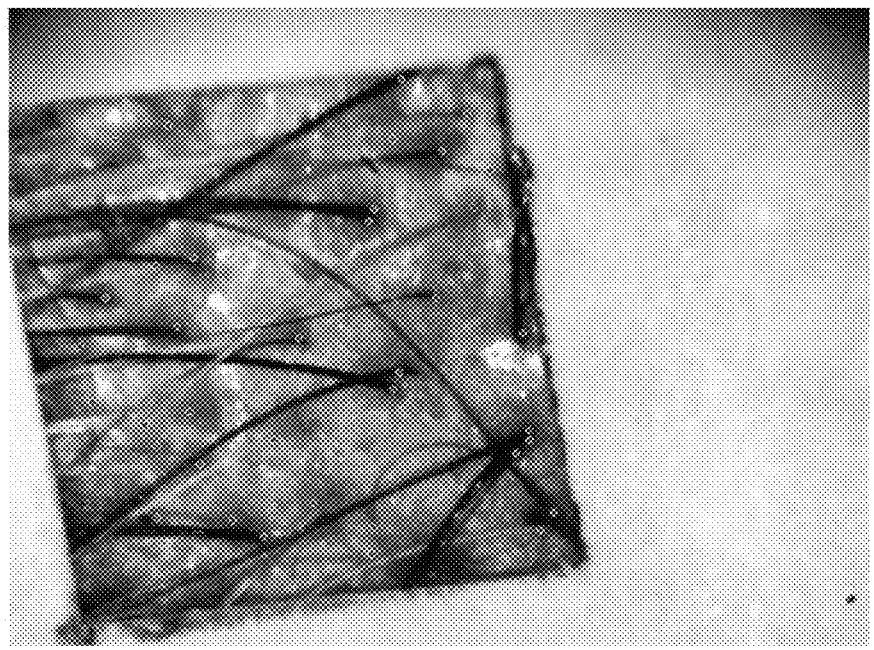
FIG. 9: (A) Photograph of ¼ cm cut-out of videomicroscope images showing vellus hair count (in red) and terminal hair count (in green).
(B) Photograph of ¼ cm cut-out of videomicroscope image showing assessment of mean hair shaft diameter. All measurements shown were multiplied by a factor of 2.77 for conversion to microns.
Figure 9B:
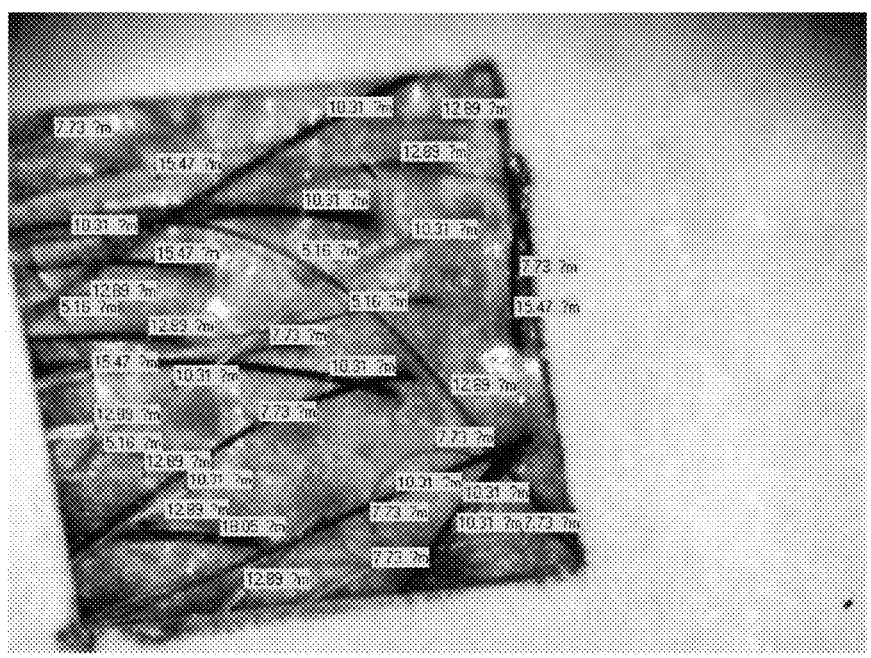

FIGS. 9(A) shows a photograph of ¼ cm cut-out of videomicroscope images showing vellus hair count (in red) and terminal hair count (in green) and 9(B) shows a photograph of ¼ cm cut-out of videomicroscope image showing assessment of mean hair shaft diameter. All measurements shown were multiplied by a factor of 2.77 for conversion to microns.

Subjective evaluation of clinical and videomicroscopic photographs was provided by three blinded reviewers. All images were randomized prior to grading so the reviewers did not know which was before or after. The results of the clinical photograph evaluation are provided in Table 8.

TABLE 8

| Patient | Reviewer 1 | Reviewer 2 | Reviewer 3 | Mean score | Delta |
|---|---|---|---|---|---|
| 1. Before | 4 | 4 | 6 | 4.67 | Increase |
| After | 7 | 7 | 7 | 7.00 | |
| 2. Before | 9 | 10 | 10 | 9.67 | Same |
| After | 9 | 10 | 10 | 9.67 | |
| 3. Before | 4 | 6 | 7 | 5.67 | Decrease |
| After | 5 | 6 | 4 | 5.00 | |
| 4. Before | 7 | 5 | 7 | 6.33 | Same |
| After | 7 | 5 | 7 | 6.33 | |
| 5. Before | 5 | 6 | 5 | 5.33 | Increase |
| After | 6 | 7 | 6 | 6.33 | |
| 6. Before | 8 | 7 | 7 | 7.33 | Increase |
| After | 8 | 8 | 9 | 8.33 | |
| 7. Before | 5 | 5 | 6 | 5.33 | Increase |
| After | 5 | 5 | 7 | 5.67 | |

Figure 10:
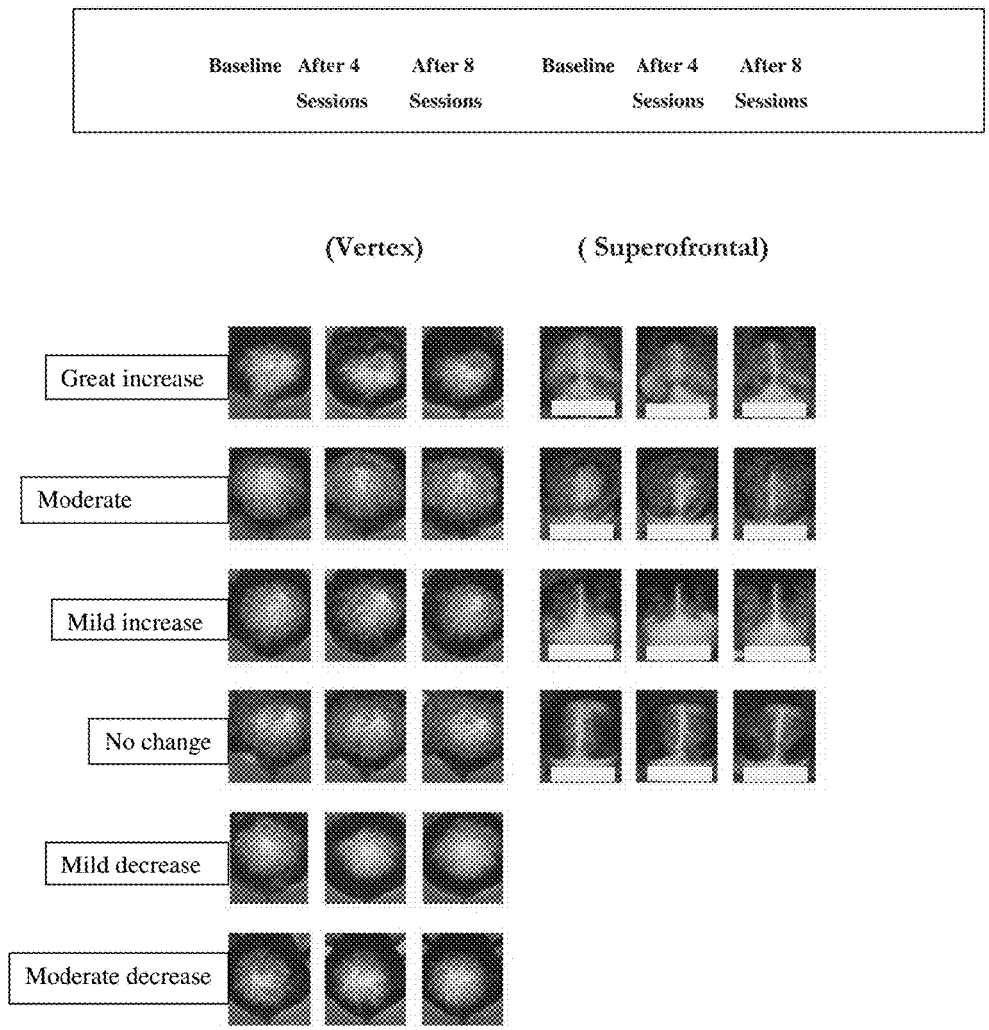
FIG. 10: Representative global photographs of patients at baseline and after 4 and 8 sessions of treatment. Changes in hair growth relative to baseline were rated by the expert panel.

There was an increased score for 71% patients, a decreased score for 10% patients, and no change in score for 19% patients. The videomicroscopic photographs were also randomized and scored from 1 to 10, in a way that the reviewers did not know whether images were before or after. The patients each had videomicroscopic photographs (taken at 15 cm and 20 cm, at baseline and after 4 and 8 sessions). FIG. 10 shows the representative global photographs of patients at baseline and after 4 and 8 sessions of treatment. An expert panel rated the changes in hair growth relative to baseline.

Figure 11:
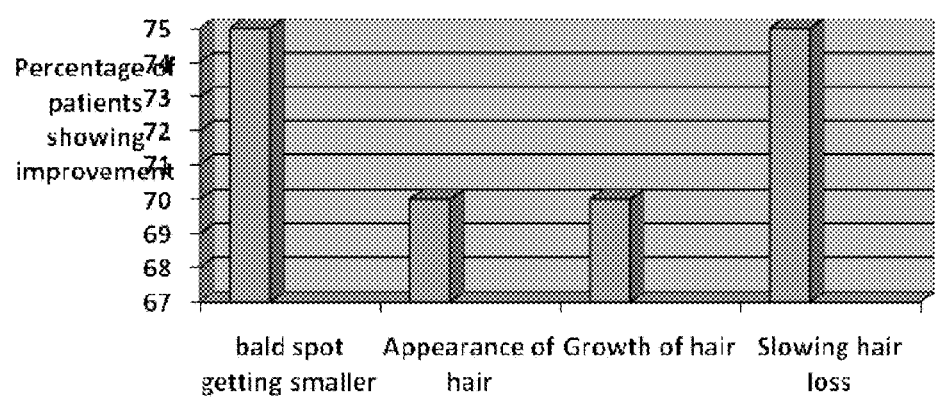
FIG. 11: Percentages of patients reporting improvement in hair growth on final scoring of patient self assessment questionnaire.
Figure 12:
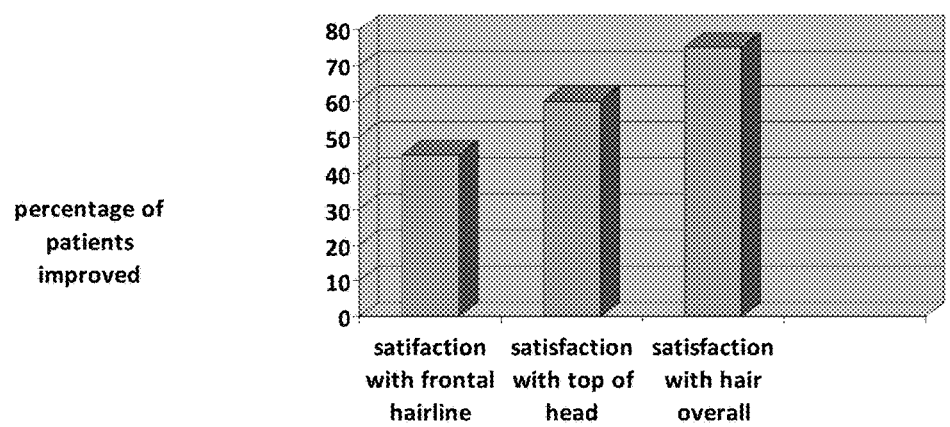
FIG. 12: Satisfaction with appearance of hair on final scoring of patient self assessment questionnaire.

Finally an overall opinion of the patients was assessed. It was observed that 75% patients believed it was helping treat their hair loss, 20% patients did not see any benefit and remaining 5% were not sure. The proportion of patients reporting improvement from baseline after 8 sessions is depicted in FIGS. 11 and 12.

The treatment was effective in improving the appearance of scalp hair and slowing the loss of hair in men and women with patterned hair loss. Significant improvement in hair growth with therapy was evident as early as after 4 sessions for all measured endpoints. After 8 sessions, global photographs showed improvement from baseline for 71% patients, a decreased score for 10% patients, and no change in score for 19% patients. The findings of this study suggest that the beneficial clinical effects of this therapy are similar in men and women, across different age groups, and in patients irrespective of the presence of metabolic disorders like diabetes, hypertension, hypercholesterolemia etc. Moreover, results indicate that therapy was also effective in controlling hair loss in 4 post hair transplant patients.

While the present invention has now been described and exemplified with some specificity, it is not intended to be limited to the details shown, and those skilled in the art will appreciate the various modifications, including variations, additions, and omissions, that may be made in the forms and details of the device illustrated and in its operation than what has been described. Accordingly, it is intended that these modifications also be encompassed by the present invention and that the scope of the present invention be limited solely by the broadest interpretation that lawfully can be accorded to the appended claims. From the foregoing it will be appreciated that although specific embodiments of the invention have been described herein for the purpose of illustration, various modifications can be made by those skilled in the art without departing in any way from the spirit of the present invention.

Without further analysis, the above description so fully reveals the gist of the present invention that others can, by applying current knowledge, readily adapt it for various applications without omitting features that, from the standpoint of prior art, fairly constitute essential characteristics of the generic or specific aspects of this invention.

We claim:

1. An intradermal pharmaceutical composition for injection into the scalp of a person for improving the bodily appearance of hair comprising:
   a) vascular endothelial growth factor in an amount ranging from 0.1 mg/L-10 mg/L, Basic fibroblast growth factor in an amount ranging from 0.1 mg/L-5 mg/L, Insulin like growth factor in an amount ranging from 0.1 mg/L-5 mg/L, Keratinocyte growth factor in an amount ranging from 0.1 mg/L-10 mg/L, and Thymosin β4 in an amount ranging from 0.001 mg/L-1 mg/L;
   b) Copper tripeptide 1 in an amount ranging from 1 mg/L-100 mg/L;
   c) an additional component selected from the group consisting of vitamins, minerals, amino acids, nucleic acids, and mixtures thereof in an amount effective to treat hair loss by stimulating hair follicles and promoting hair growth, where such hair growth improves the bodily appearance of the said person; and
   d) a sterile injectable vehicles;
   wherein at least one of said vascular endothelial growth factor, said basic fibroblast growth factor, said insulin like growth factor, said keratinocyte growth factor, and said thymosin β4 is provided in the form of nanosomes.

2. The intradermal composition according to claim 1, wherein the additional component is selected from the group consisting of:
   a vitamin selected from the group consisting of Vitamin A, Vitamin B1, Vitamin B2, Vitamin B3, Vitamin B5, Vitamin B6, Vitamin B7, Vitamin B10, Vitamin B12, Vitamin C, Vitamin K, Vitamin I, and mixtures thereof;
   a mineral selected from the group consisting of Sodium, Potassium, Magnesium, Calcium, and mixtures thereof;
   Adenosine, Cytosine, Guanine, Thymine, or a mixture thereof; and
   an amino acid.

3. The intradermal composition according to claim 2, wherein the amino acid is an essential amino acid.

4. The intradermal composition according to claim 2, wherein the amino acid is a non-essential amino acid.

5. The intradermal composition according to claim 1, comprising vascular endothelial growth factor in an amount of 5 mg/L, Basic fibroblast growth factor in an amount of 2 mg/L, Insulin like growth factor in an amount of 2 mg/L, Keratinocyte growth factor in an amount of 1 mg/L, and Thymosin β4 in an amount of 0.01 mg/L and Copper tripeptide 1 in an amount of 10 mg/L.

6. The intradermal composition according to claim 1, wherein said sterile injectable vehicle is selected from the group consisting of saline solution, distilled water and mixtures thereof.

7. The intradermal composition according to claim 1, wherein said vascular endothelial growth factor is provided in the form of nanosomes.

8. The intradermal composition according to claim 1, wherein said basic fibroblast growth factor is provided in the form of nanosomes.

9. The intradermal composition according to claim 1, wherein said insulin like growth factor is provided in the form of nanosomes.

10. The intradermal composition according to claim 1, wherein said keratinocyte growth factor is provided in the form of nanosomes.

11. The intradermal composition according to claim 1, wherein said thymosin β4 is provided in the form of nanosomes.

12. A method of treating hair loss in a patient in need thereof, comprising intradermally injecting a pharmaceutical composition according to claim 1 into an affected area of the scalp of the patient, said intradermal pharmaceutical composition being administered in an amount effective to treat hair loss by stimulating hair follicles and promoting hair growth,
   wherein the subject has at least one of androgenetic alopecia, alopecia areata, female pattern baldness, and secondary alopecia.

13. The method of claim 12, further comprising a step of co-administering a hair growth promoting compound selected from the group consisting of minoxidil, minoxidil analogs, minoxidil derivatives anti-androgens, and 5-alpha-reductase inhibitors to the patient.

14. A method of improving the bodily appearance of hair of a person comprising injecting into an affected area of the scalp of said person a pharmaceutical composition in an amount effective to treat hair loss by stimulating hair follicles and promoting hair growth;
   said pharmaceutical composition comprising:
   a) vascular endothelial growth factor in an amount ranging from 0.1 mg/L-10 mg/L, Basic fibroblast growth factor in an amount ranging from 0.1 mg/L-5 mg/L, Insulin like growth factor in an amount ranging from 0.1 mg/L-5 mg/L, Keratinocyte growth factor in an amount ranging from 0.1 mg/L-10 mg/L, and Thymosin β4 in an amount ranging from 0.001 mg/L-1 mg/L;
   b) Copper tripeptide 1 in an amount ranging from 1 mg/L-100 mg/L;
   c) an additional component selected from the group consisting of vitamins, minerals, amino acids, nucleic acids, and mixtures thereof in an amount effective to treat hair loss by stimulating hair follicles and promoting hair growth, where such hair growth improves the bodily appearance of the said person; and
   d) a sterile injectable vehicle.

15. The method of improving the bodily appearance of hair of a person according to claim 14, wherein the step of injecting the effective amount of the pharmaceutical composition into said person is performed once in 2 to 6 weeks.

16. The method according to claim 14, wherein the additional component is selected from the group consisting of:
   a vitamin selected from the group consisting of Vitamin A, Vitamin B1, Vitamin B2, Vitamin B3, Vitamin B5, Vitamin B6, Vitamin B7, Vitamin B10, Vitamin B12, Vitamin C, Vitamin K, Vitamin I, and mixtures thereof;

a mineral selected from the group consisting of Sodium, Potassium, Magnesium, Calcium, and mixtures thereof;

Adenosine, Cytosine, Guanine, Thymine, or a mixture thereof; and an amino acid.

17. The method according to claim 14, comprising vascular endothelial growth factor in an amount of 5 mg/L, Basic fibroblast growth factor in an amount of 2 mg/L, Insulin like growth factor in an amount of 2 mg/L, Keratinocyte growth factor in an amount of 1 mg/L, and Thymosin β4 in an amount of 0.01 mg/L and Copper tripeptide 1 in an amount of 10 mg/L.

18. The method according to claim 14, wherein at least one of said vascular endothelial growth factor, said basic fibroblast growth factor, said insulin like growth factor, said keratinocyte growth factor, and said thymosin β4 is provided in the form of nanosomes.

19. The method of improving the bodily appearance of hair of a person according to claim 14, comprising the following sequence of steps;
   a. cleaning the scalp of the person with alcohol swab or surgical spirit;
   b. treating the affected area of the scalp by intradermally injecting the pharmaceutical composition in an effective stimulatory amount to treat alopecia.

20. The method of claim 19, further comprising a further step of administering a hair growth promoting compound to the person, said hair growth promoting compound being selected from the group consisting of minoxidil, minoxidil analogs, minoxidil derivatives, anti-androgens, and 5-alpha-reductase inhibitors.

\* \* \* \* \*